United States Patent
Lemchen

[11] Patent Number: 5,890,892
[45] Date of Patent: Apr. 6, 1999

[54] ORTHODONTIC BRACKET WITH NON-ADHESIVE MOLDABLE BASE AND METHOD

[76] Inventor: Marc S. Lemchen, 553 Park Ave., New York, N.Y. 10021

[21] Appl. No.: 789,312
[22] Filed: Jan. 23, 1997
[51] Int. Cl.[6] ........................................ A61C 3/00
[52] U.S. Cl. .............................. 433/9; 433/3; 206/63.5; 206/368
[58] Field of Search ................... 433/9, 8, 3, 4; 206/63.5, 368, 369

[56] References Cited

U.S. PATENT DOCUMENTS

| | | | |
|---|---|---|---|
| 3,936,939 | 2/1976 | Faunce | 433/9 |
| 4,657,508 | 4/1987 | Dellinger | 433/9 |
| 5,007,827 | 4/1991 | DiFranco | 433/4 |
| 5,015,180 | 5/1991 | Randklev | 433/9 |
| 5,221,202 | 6/1993 | James | 433/9 |
| 5,354,199 | 10/1994 | Jacobs et al. | 433/9 |
| 5,538,428 | 7/1996 | Staubli | 206/63.5 |

*Primary Examiner*—John J. Wilson
*Attorney, Agent, or Firm*—Daniel L. Dawes

[57] ABSTRACT

A dental bracket having a non-adhering, moldable base, wherein the moldable base is conformed to the surface of the tooth to which it is to be adhered. A very thin layer of dental adhesive interposed between the moldable base and the tooth (by coating of any or both of the tooth and moldable base—preferably the tooth) effects full adherence of the bracket to the tooth. The base material is fully cured by normal curing methods such as by UV or other wavelength light activation. Use of a non-tacky, bondable plastic membrane (or coating or use of a thin inert interposition material which is non-tacky and bondable) bonded to the base material (and which is conformed with the molding of the base material), facilitates application of a bracket with an applicator. A bracket applicator and package suitable for use with the dental bracket of the present invention is also described.

8 Claims, 4 Drawing Sheets

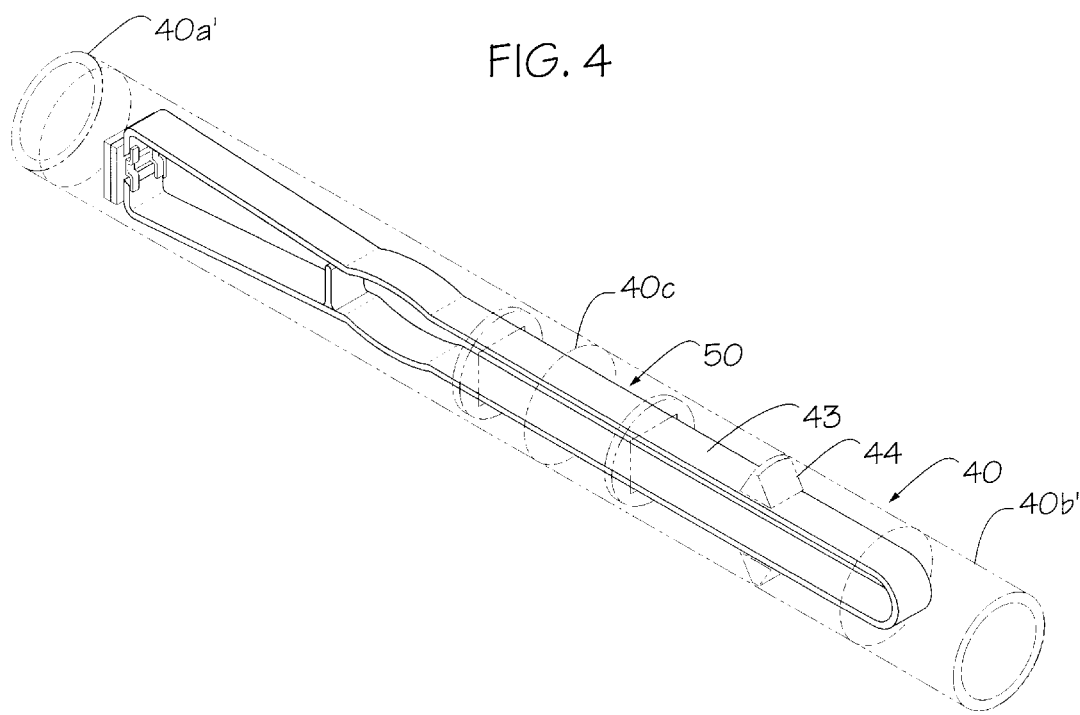
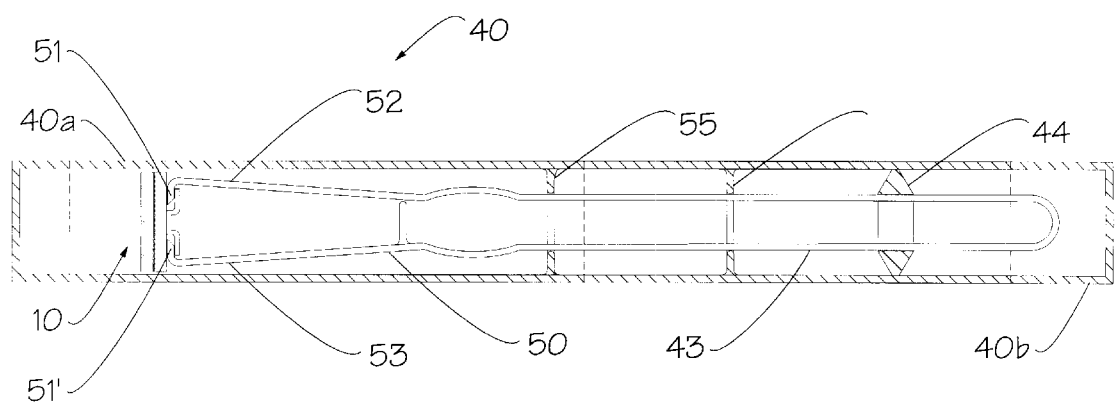

ORTHODONTIC BRACKET WITH NON-ADHESIVE MOLDABLE BASE AND METHOD

FIELD OF THE INVENTION

This invention relates to dental orthodontic brackets which are removably but firmly adhered to a patient's teeth in order to temporarily install orthodontic braces for corrective teeth orientation. The invention particularly relates to dental brackets having integral base elements which are conformed to teeth surfaces.

BACKGROUND OF THE INVENTION

Orthodontic correction of teeth for proper orientation generally requires the utilization of orthodontic braces which are designed to gradually force the teeth into a pre-determined corrected configuration. These braces are usually configured as tightly drawn wires attached to the teeth either peripherally on the external or visible side of the teeth or, for cosmetic reasons, against the internal surface of the teeth.

In order to keep the braces or wires in position, it is necessary to anchor the wires to a fixed position on the teeth and this is effected by means of dental bracket, i.e., wire holding brackets which are firmly attached to the surface of the teeth. In order to ensure that the brackets remain in position on the teeth, particularly with the constant stress placed on them, it is the practice to provide the bracket with a planar (i.e. loosely reflecting the shape of an average tooth surface) extension portion, or bottom, having a mesh brazed thereon and to which a tooth-conforming base material is attached. The base is closely conformed to a pre-selected portion of the tooth surface, which is rarely planar but is usually irregularly curved, and then the base, and the bracket, are adhered to the tooth. The conformed base assumes a full length area of attachment which the planar bracket itself cannot.

A common method for ensuring a proper attachment initially entails preparing a plaster of paris casting of the teeth. A hardened, molded base for fixing the dental bracket in place is then formed from the casting to serve as the base of the bracket, when it is applied to the tooth. The base is adhered to the bracket itself or to an extension of the bracket which is in the form of a mesh for enhanced bonding therebetween. The bracket and base are then adhered to the individual teeth.

The base, with attached bracket, is adhered to a tooth by a thin coating of a liquid dental adhesive which is brushed on one or both of the tooth surface and the engaging surface of the base, prior to actual use. The adhesive is a standard adhesive which, because of the preformed nature of the base, may be immediately adherent. While this method provides a well seated bracket, it requires additional steps and procedures in separately casting a mold prior to actual placement of the bracket on the tooth.

With a different and increasingly popular type of one step dental bracket, a dental bracket is provided, by welding thereto of a relatively rigid, generally tooth-conforming metal strip having a mesh thereon and onto which a relatively thick layer of a moldable, paste adhesive (as characterized by the manufacturer and which requires separate activation to permit for molding conformation prior to adhesion) has been loaded by the manufacturer. In use, the dental bracket is removed from its packaging, a release paper or plastic film is peeled off the manufacturer-applied adhesive surface, and the bracket base is pressed against the surface of the teeth to which it is to be adhered. The pre-loaded adhesive is relatively thick and moldable whereby compressive placement on the teeth causes the adhesive to conform to the normally irregular teeth surfaces and to fill in any gaps between the rigid base member and the teeth surfaces. Once the adhesive is properly conformed to a tooth, it is activated for adhesion (and hardened in place) by, for example, application of UV light irradiation to complete the adhesive placement of the bracket.

While such adhesive pre-loaded dental brackets are popular because of their convenience and simple application (even with use of a complementary adhesive which is often used on the teeth prior to the molded placement of the paste adhesive base), the use thereof requires the application of a relatively thick layer of paste adhesive, for molding conformity. This excessive thickness of adhesive layer however entails several drawbacks. As with adhesive application in any field, e.g., wood joints in carpentry, the weakest part of an adhesion bond between adhered rigid members, is the adhesive itself and accordingly thickness of the adhesive layer is usually minimized, where possible, for best and strongest adhesion properties. However, when the adhesive is thickened for a specific purpose, e.g., for gap filling, the integrity of the adhesive bond may be lessened. Thus, with the common adhesive pre-loaded dental brackets, the gap filling thickness of the adhesive (thicker than needed for adhesion), affords considerable stress points in the adhesive, at which the adhesive itself may split, with possible dislodgement of the bracket. If the base material has a greater shear strength than that of the adhesive, then use of a thickened adhesive layer works to reduce the overall integrity of the bond.

In addition and possibly of greater moment, is the fact that while application time may be initially lessened, this is more than offset by the additional labor and time required for the complete removal of the thick adhesive layer (at the time when the bracket is no longer needed, i.e., when the orthodontia is to be removed).

SUMMARY OF THE INVENTION

It is therefore an object of the present invention to provide a single step application dental bracket with means for minimizing the amount of adhesive required for anchoring a dental bracket, for orthodontic wires or appliances, to a tooth surface.

It is a further object of the present invention to provide a dental bracket having a moldable and curable but not adhesive base which is partially uncured prior to actual use, at which time the base itself is conformed to the surface of a tooth and wherein adherence to the tooth is effected by a thin, non-gap filling, minimal coat of an activatable adhesive having been applied to either or both of the surface of the base and the surface of the tooth, prior to the molding conformation but after removal from the manufacturer's packaging.

It is another object of the present invention to utilize an A–B type of adhesive with one of the components thereof being placed on the base and the other on the tooth and adhesive activation is effected by compression contact between the components, with the base material being fully cured thereafter.

It is yet another object of the present invention to provide a membrane film, coating or other non-adhesive interface to which the adhesive is applied, which film or interface is interposed between the molded base and the tooth.

It is still yet another object of the present invention to provide an applicator and handling means for the dental bracket of the present invention.

The present invention comprises an orthodontic bracket for use in anchoring orthodontic wires or appliances to teeth, the bracket comprises means for conforming the bracket to the surface of a tooth and means for adhering the bracket to the tooth. The bracket is comprised of a bracket member having an attached base member comprised of a substantially non-adhering, moldable, curable material, most commonly a polymer or polymeric material which is partially cured prior to application to a tooth and whereby it remains moldable for full conformation with a surface of the tooth. A liquid adhesive coating is interposed between the base material and the tooth, prior to molding of the base material into conformity with the surface of the tooth, with the liquid adhesive, when cured, providing the means for adhering the bracket to the tooth.

The present invention further comprises a method for adhering a dental bracket to a tooth with full conformity to a surface of the tooth, with minimal use of adhesive, said method comprising the steps of:

a) providing a bracket member with a moldable, curable, non-adhesive base material, with said base material being at most only partially cured prior to application to a tooth, b) coating at least one of the base material and tooth surface with a liquid dental adhesive material, c) applying the base material to the tooth surface and molding the base material into full conformity therewith, and d) completing curing of the base material and activating the dental adhesive while the base material is in conformity with the tooth surface.

The present invention also preferably comprises a unique combination dental bracket; holder-applicator member for the releasable holding thereof; and enclosure packaging for the bracket and holder-applicator member. The holder comprises means for fixedly holding the bracket as well as means, remote from the bracket, for remotely effecting removal thereof from the holder. The enclosure packaging comprises a closed, generally tubular package having separable segments thereof for access to the holder and dental bracket contained therein and in a preferred embodiment cooperatively provides a combination of package and manipulating handle for the holder.

The above objects and other objects, features and advantages of the present invention will become more evident from the following discussion and drawings in which:

SHORT DESCRIPTION OF THE DRAWINGS

FIGS. 4 and 5 depict an integrated package and applicator suitable for use with the dental bracket of the present invention.

DETAILED DESCRIPTION OF THE INVENTION

Figure 1:
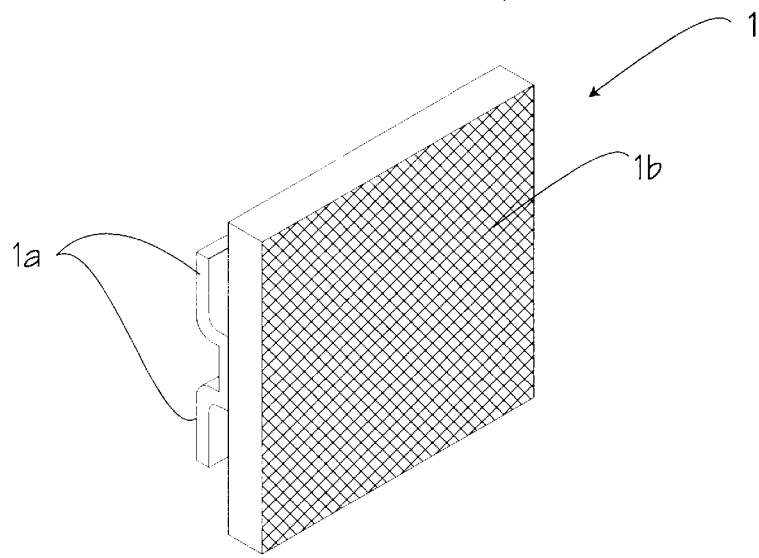
FIG. 1 depicts a bottom isometric view of a dental bracket of the prior art with a mesh-like bottom portion and without the moldable base of the present invention.

Generally the present invention comprises a dental bracket for use in anchoring orthodontia to teeth, with means for conforming the bracket to the surface of the teeth and means for adhering the bracket to the teeth. The bracket, adapted to fixedly hold an orthodontic wire therein, is comprised of a bracket member with a standard base of plastic, mesh or ceramic material which is mechanically or chemically bonded to a base material comprised of a moldable, substantially non-adhering polymer which is curable such as with specific wave length light, heat or chemical catalyst for hardening. Examples of materials suitable for the base material include a material available from the DENTSPLY Company, and designated as a Triad material. Generally included are non-adhesive denture materials made of methyl methacrylate, polycarbonate, acrylate polymers, and the like. The bracket with base material is packaged in a light proof package with the base material, without adhesive thereon.

In use, the bracket is removed from its packaging, preferably with a protective peelable layer of release paper or plastic (e.g., mylar) remaining thereon and held by a slight residual tackiness or by elements of an applicator which will be described. In a preferred embodiment, the base, having been only partially cured, is, in one embodiment, coated with an activatable adhesive and then applied to the tooth to which it is to be adhered (the tooth surface having been coated with the complement to the adhesive such as an A–B type mixing epoxy).

Alternatively, only the tooth is coated with a one part liquid adhesive. In all embodiments the base material itself is then molded into full conformity with the tooth (i.e., the base material providing the in situ gap filling), while allowing a proper minimal size interface between the tooth and the base material for the liquid adhesive.

The tooth conforming surface of the bracket base and/or the tooth surface is coated with a thin coating of dental adhesive, only sufficient to provide the requisite adhesion, with adhesion application being by a simple brush-on or spray of the adhesive. The adhesive and base material are then cured to complete both the molding and adhering processes.

It is preferred that the adhesive used be of an activatable type whereby, when the bracket is properly positioned, molded and fully conformed, the adhesive is activated to effect the adhesion. A two part adhesive may be used, with part A being applied to the bracket base and part B applied to the tooth and wherein the adhesive of both parts is activated such as by a laser curing light when the base of the bracket is positioned and fully molded-fitted onto the surface of the tooth.

Most preferable is a one part adhesive which is applied to only the surface of the tooth. Examples of such materials include the activatable and non activatable adhesives available from the Unitek division of the 3M Corporation and directly from the 3M Corporation itself, under the trademarks Transcend and Concise.

In an alternative embodiment, the light cured base material is enclosed or covered with a non-adhesive, non tacky, bondable plastic membrane, or other inert interposition material such as a thin fabric or inert coating, which forms an interface with the bracket and also an adhesive interface with the tooth, while allowing the base material to be molded into conformity with the tooth surface.

In order to effect mechanical connection to the base member the otherwise non-adhering plastic membrane is preferably ridged on its interface with the base member and cured therewith to effect a mechanical bond thereby. The membrane or coating may also be discontinuous such as by being pre-perforated to enhance the mechanical bond with base material oozing therethrough, when compressed, to bond directly to the tooth. Alternatively, a coating may become perforated or partially broken apart under pressure caused by forcing the bracket against the tooth, thereby allowing the base material to at least partially come into direct contact with the adhesive.

The advantage of utilizing a plastic membrane or other material interface lies in its permitting the base material to be "pressed" into the mesh of the bracket without sticking to an applicator. It is noted in this regard that while the base member is considered not to have adhesive or adhering properties, it normally has some tackiness which can affect ready removal from an applicator but which tackiness, by itself, is insufficient to effect a requisite bonding with a tooth surface.

In order to avoid problems with placing the brackets on a bracket holder in a manner which will permit the very thin coat of adhesive to contact the tooth surface before release of the bracket holder (thereby avoiding the bracket from being released and falling into the mouth) it is preferred, in an embodiment of the present invention, that the bracket be packaged for immediate use with its own integrated holder as an applicator in its own packaging. The applicator member packaging is preferably in the form of a closed pen-like tube made of inexpensive cardboard or plastic with the bracket, whether uncoated or precoated with adhesive, being retained by the integrated holder element contained therein.

The integrated holder element can be inexpensively, yet effectively made of cast or molded plastic, and, for convenience the integrated holder may be color coded by arch or arch and tooth. Brackets for premolars and molars are mounted offset by 90 degrees for facilitated placement. The integrated holder element is comprised of an end terminating in split arms which engage the bracket. A molded hinge in one of the arms permits the application of pressure thereon to result in release of the bracket from the holder.

For use, the packaging tube is opened, with the retained bracket and integrated holder externally extended for removal and use. The means for extending the holder retained bracket from the packaging, may vary. Thus, the tube may have openings at both ends with the bracket holder being pushed from one end for extension out of the other end for removal. Alternatively, the bracket is provided with a holding tab which is removed to release the holder and bracket out of one end. The tube may be made frangible to be controllably, centrally broken for access to the holder and bracket by removal of both ends (or removal of the bracket end while retaining the other end as part of the handle for the holder).

In a preferred embodiment of the holder and packaging, the holder and packaging are made to operate as a one-piece package and holder. In this embodiment the packaging and holder are provided with co-operative stop elements whereby the bracket is exposed (by removal of a portion of the packaging adjacent the holder end for external access thereto. The holder is pushed to a stop element within the packaging whereby the bracket is exposed for proper tooth placement. At the same time, the release hinge of the holder is aligned with a compressible or marked portion of the package where a squeeze of the packaging effects disengagement of the holder from the bracket.

DETAILED DESCRIPTION OF THE DRAWINGS AND THE PREFERRED EMBODIMENTS

With specific reference to the drawings, in FIG. 1, a prior art dental bracket 1 is comprised of the hook shaped brackets 1a and a rigid integrated bottom with a mesh-like surface 1b, for usual bonding with a prior art layer of activatable paste adhesive (not shown).

Figure 2A:
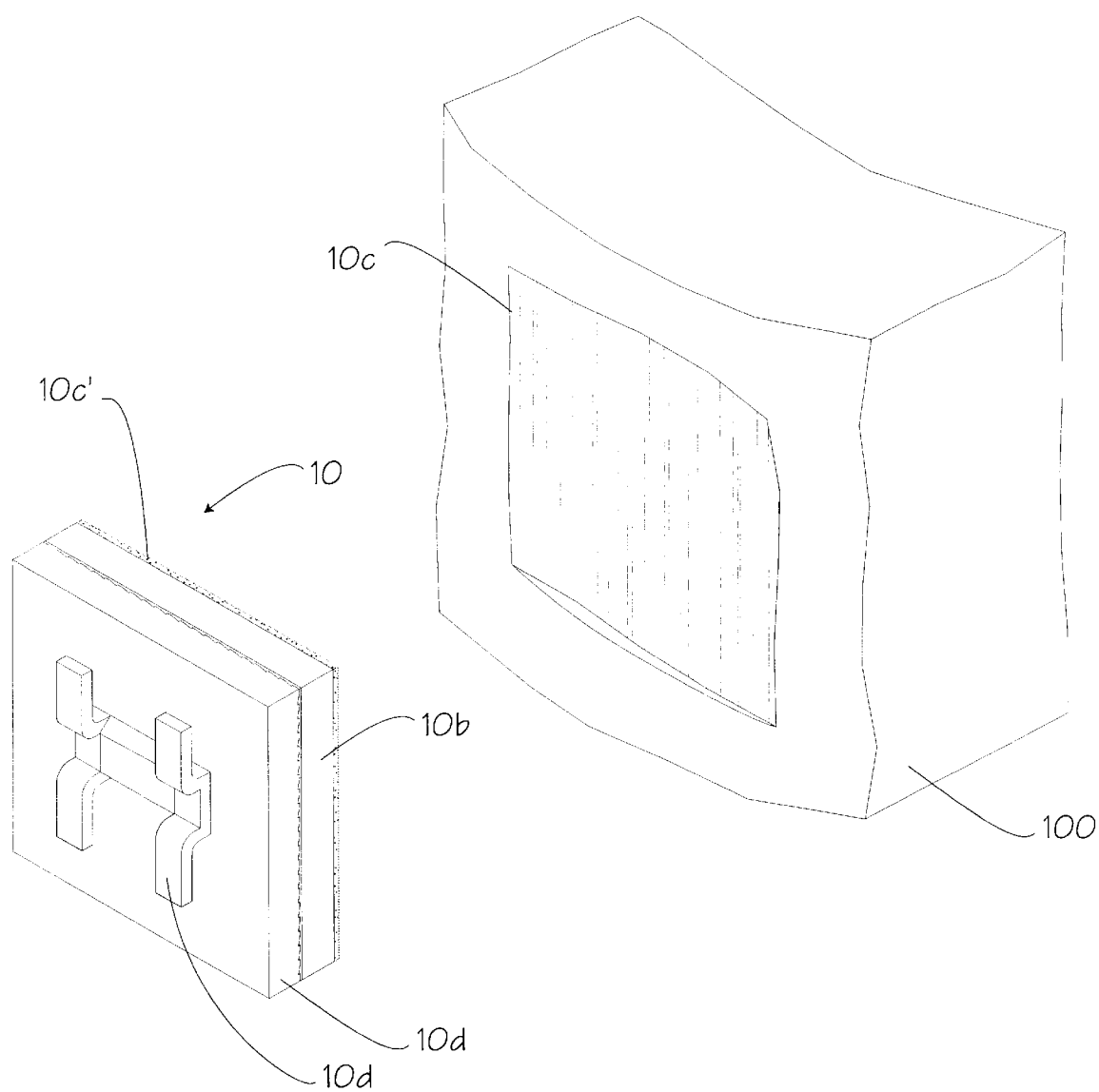
FIG. 2a is a partial section side view of a bracket according to the present invention with a moldable non-adhering base bound to the mesh-like bottom and with the bracket shown prior to emplacement on a portion of a tooth having a liquid adhesive coating thereon.
Figure 2B:
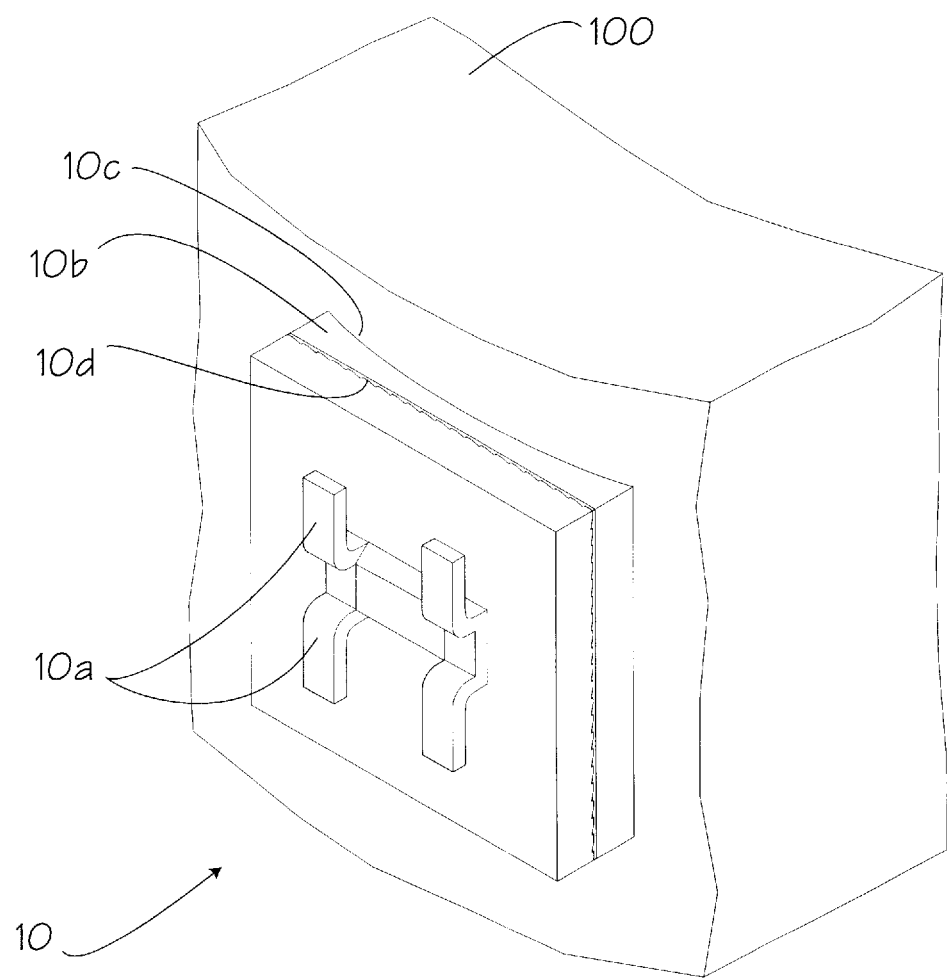
FIG. 2b is an isometric depiction of the dental bracket of the FIG. 2a having been shape molded and adhered to the tooth via the liquid adhesive layer.

As shown in FIGS. 2a and 2b the dental bracket 10 of the present invention comprises bracket 10a with the mesh-like surface 10d having been bonded with partially cured non-adhesive polymeric base 10b (e.g. of denture material). The bracket 10 is shown in FIG. 2a as being placed on a portion of tooth surface 100 which was pre-coated with a thin layer of liquid adhesive 10c. As shown in phantom in FIG. 2a, base 10b may also be coated with a thin layer of adhesive component 10c', when adhesive components 10c and 10c' are chemically complementary. The adhesive components 10c and 10c' are not gap filling. Instead, as shown in FIG. 2b, partially cured non-adhesive base 10b is sufficiently moldable to conform to tooth surface 100a, with room for the thin liquid adhesive layer 10c (or 10c and 10c'). Base material 10b is molded to the contour of the rounded tooth 100 to provide full contact for maximum adhesion between the base material 10b and tooth 100 via adhesive 10c (or 10c and 10c'). The resultant bond is strong, but with minimized residual adhesive material for removal.

Figure 3A:
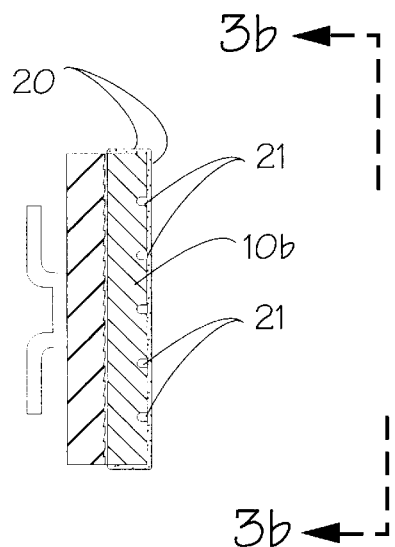
FIG. 3a is a partial section side view of a second embodiment of the dental bracket of the present invention.
Figure 3B:
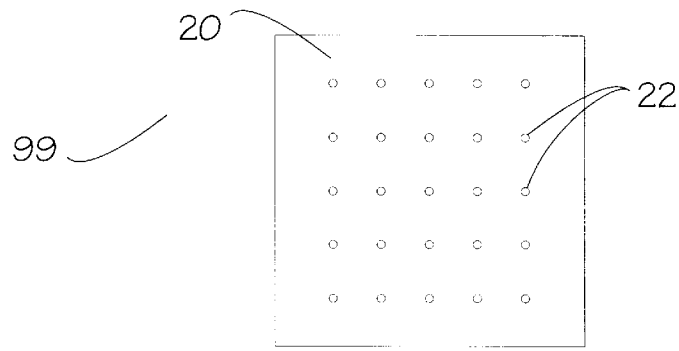
FIG. 3b is a bottom view of the bracket of FIG. 3a taken along line 3b—3b.

A modified embodiment of the present invention is shown in FIG. 3a wherein polymeric base 10b is covered with plastic membrane 20 (represented as such but which can also be a fabric, or any other bondable but non-adhesive material or coating), with the adhesion by the adhesive material 10c being effected with and through the plastic membrane 20. The interface and bonding between the membrane 20 and polymeric base 10b is mechanically enhanced with ridges 21 in the membrane, situated at the interface, which ridges are bonded to the base with curing of the base. Perforations 22 in the membrane 20 permit the adhesive to directly contact portions of the base 10b for enhanced bonding and reduction of the possibility of forced separation of the membrane from the base material under stress.

The applicator package 40 (made of a molded plastic or cardboard tube) shown in FIGS. 4 and 5, provides both packaging of a bracket 10 and an integral holder 50 therefor for application to a tooth 100. The bracket 10 is held between the ends 51 and 51' respectively of split arms 52 and 53. Release of the bracket from between the ends, when the bracket is being placed on a tooth, is effected by pressing hinge point 55 which causes split arm 52 and end 51 to swivel up sufficiently to release the bracket.

With a common configuration as shown, opening of applicator package 40 for application access to the holder and the bracket is effected in the various manners shown. Thus, removal of package ends 40a and 40b exposes holding end 43 with bracket 10 and the end of holder 50, whereby a push on the holder end serves to extend the bracket from the other end for removal. With such embodiment, stop elements 44 and 46 of the holder and the package limit travel of the holder to simply expose the bracket sufficiently for application without removal of the holder from the package. Activation, i.e., removal of the bracket is effected by compression of the package on a marked point aligned with the hinge 55, see FIG. 5 to compress the hinge, with removal as described.

Alternatively, the package 40 may be opened at center score line 40c, which permits removal of extended front and rear ends 40a and 40b' for removal of the holder and bracket from package 40.

Use of plastic membrane 20, as described, provides better control of the bracket placement since it permits immediate release when required, as a result of its lack of residual tackiness, which is a characteristics of moldable polymeric base materials.

It is understood that the above description, drawings and examples of dental brackets and applicators are merely illustrative of the present invention and that changes may be made in structure and components, including the chemical nature and properties of the base material, interposition materials and/or coatings, adhesives and the like, without departing from the scope of the present invention as defined by the following claims.

What is claimed is:

1. A prepackaged dental bracket for use in anchoring any of orthodontic appliances or brackets to teeth, comprising:
   means for conforming the bracket to the surface of a tooth; and
   means for adhering the bracket to the tooth, said means for conforming and said means for adhering being combined together to form said prepackaged bracket prior to application of said bracket to said tooth,
   wherein said prepackaged bracket is comprised of a universally shaped bracket member having a base member comprised of a substantially non-adhering, moldable, curable material which is partially cured prior to application to a tooth so that it remains moldable for full conformation with a surface of the tooth, thereby comprising said means for conforming the prepackaged bracket to the surface of the tooth, and
   wherein a liquid adhesive coating, is to be interposed between the base material and the tooth, prior to molding of the base material into conformity with the surface of the tooth, with said liquid adhesive coating, when cured, providing the means for adhering the prepackaged bracket to the tooth.

2. The dental bracket of claim 1, wherein the base material is residually tacky prior to complete curing thereof, and wherein the base material is covered with and bonded to an element which is one of the following:
   a bondable, non-tacky, plastic membrane;
   a bondable, non-tacky inert coating; or
   a bondable, non-tacky thin layer of an inert interposition material,
   such that said element is at least partially interposed between the base material and the liquid adhesive.

3. The dental bracket of claim 1, further comprising said liquid adhesive coating and wherein the liquid adhesive coating is applied only to the tooth, prior to molding of the base material into conformity with the surface of the tooth.

4. A dental bracket for use in anchoring any of orthodontic appliances or brackets to teeth, comprising:
   means for conforming the bracket to the surface of a tooth; and
   means for adhering the bracket to the tooth,
   wherein said bracket is comprised of a bracket member having a base member comprised of a substantially non-adhering, moldable, curable material which is partially cured prior to application to a tooth whereby it remains moldable for full conformation with a surface of the tooth, thereby comprising said means for conforming the bracket to the surface of the tooth, and
   wherein a liquid adhesive coating, is to be interposed between the base material and the tooth, prior to molding of the base material into conformity with the surface of the tooth, with said liquid adhesive coating, when cured, providing the means for adhering the bracket to the tooth
   wherein the base material is residually tacky prior to complete curing thereof, and wherein the base material is covered with and bonded to an element which is one of the following:
   a bondable, non-tacky, plastic membrane;
   a bondable, non-tacky inert coating; or
   a bondable, non-tacky thin layer of an inert interposition material,
   such that said element is at least partially interposed between the base material and the liquid adhesive,
   wherein said element is discontinuous, whereby the liquid adhesive is in contact with both the base material and said element.

5. A method for adhering a prepackaged dental bracket to a tooth with full conformity to a surface of the tooth, with minimal use of adhesive, said method comprising the steps of:
   a) providing a universally shaped bracket member with a moldable, curable prepackaged base material, with said prepackaged base material being at most only partially cured prior to application to a tooth, said prepackaged base material being combined with said bracket member prior to being supplied to a user to apply to said tooth,
   b) coating by user application at least one of the base material and tooth surface with a liquid dental adhesive material,
   c) applying by user application the base material to the tooth surface and molding the base material into full and self-retained conformity therewith by pressing said base material against said tooth to deform said base material into intimate conformity with said tooth, said base material being completely deformable without any tendency to resume its predeformed shape, and
   d) completing curing of the base material and activating the dental adhesive while the base material is in conformity with the tooth surface.

6. A method for adhering a dental bracket to a tooth with full conformity to a surface of the tooth, with minimal use of adhesive, said method comprising the steps of:
   providing a bracket member with a moldable, curable base material, with said base material being at most only partially cured prior to application to a tooth,
   coating at least one of the base material and tooth surface with a liquid dental adhesive material,
   applying the base material to the tooth surface and molding the base material into full conformity therewith, and
   completing curing of the base material and activating the dental adhesive while the base material is in conformity with the tooth surface,
   wherein one of a bondable and non-tacky plastic membrane, coating and inert interposition material layer is bonded to the base material prior to the coating of at least one of the base material and tooth surface with the dental adhesive material.

7. A combination holder-and-applicator member for the releasable holding of said bracket; and for light tight enclosure packaging of the bracket; said holder-and-applicator member comprising means for fixedly holding the bracket and means, remote from the bracket, for remotely effecting removal thereof from the holder-and-applicator member, and
   wherein the enclosure packaging comprises a closed, light tight, generally tubular package having separable segments thereof for access to the holder-and-applicator and dental bracket contained therein, so that said holder-and-applicator can be extended out of said tubular package, said bracket applied to said tooth and released from said holder-and-applicator without the need to touch said bracket or to remove any covering from said bracket.

8. The combination of claim 7, wherein the enclosure packaging and holder comprise interactive stop means wherein the holder is only movable for a predetermined distance, within the packaging, to effect extension of the dental bracket outside of the enclosure, and wherein the enclosure packaging and holder comprise release means for remotely effecting release of the bracket from the holder.

* * * * *